United States Patent [19]

Emmons

[11] 4,024,117
[45] May 17, 1977

[54] HYDROCURABLE COMPOSITIONS OF HYDROXY(POLYALKYLENECARBONYLOXY)-ALKYLENEOXAZOLIDINE AND AN ISOCYANATE

[75] Inventor: William D. Emmons, Huntingdon Valley, Pa.

[73] Assignee: Rohm and Haas Company, Philadelphia, Pa.

[22] Filed: Apr. 21, 1975

[21] Appl. No.: 569,739

Related U.S. Application Data

[62] Division of Ser. No. 425,007, Dec. 14, 1973, Pat. No. 3,912,691.

[52] U.S. Cl. .................... 260/78.3 R; 260/307 F; 260/307 FA
[51] Int. Cl.² ........................................ C08G 63/02
[58] Field of Search ..... 260/78.3 R, 307 F, 307 FA

[56] References Cited

UNITED STATES PATENTS

| | | | |
|---|---|---|---|
| 3,729,446 | 4/1973 | Holub et al. | 260/78.3 R |
| 3,730,807 | 5/1973 | Smith et al. | 260/78 3 R |
| 3,786,028 | 1/1974 | MacDonald | 260/78.3 R |
| 3,896,303 | 7/1975 | Gerkin et al. | 260/78.3 R |

*Primary Examiner*—M. J. Welsh
*Attorney, Agent, or Firm*—Terence P. Strobaugh; George W. F. Simmons; Robert A. Doherty

[57] ABSTRACT

Hydrocurable compositions of a hydroxy(polyalkylenecarbonyloxy)alkyleneoxazolidine and a polyfunctional isocyanate are disclosed. The compositions are useful in forming films, paints, coatings, fibers, seamless flooring, coatings, impregnants and adhesives for natural and synthetic materials. The compositions are prepared by treating a hydroxy(polyalkylenecarbonyloxy)alkyleneoxazolidine with a polyfunctional isocyanate or by treating a bisoxazolidine isocyanate prepolymer with a polyfunctional isocyanate.

6 Claims, No Drawings

HYDROCURABLE COMPOSITIONS OF HYDROXY(POLYALKYLENECARBONYLOXY)-ALKYLENEOXAZOLIDINE AND AN ISOCYANATE

This is a division of application Ser. No. 425,007, filed Dec. 14, 1973, and now U.S. Pat. No. 3,912,691.

This invention relates to a novel composition comprising a hydroxy(polyalkylenecarbonyloxy)alkyleneoxazolidine and a polyfunctional aliphatic or aromatic isocyanate which has an outstanding balance of speed of cure relative to its stability. The composition cures in the presence of moisture to afford tough chemically resistant polymeric materials. This invention also relates to the novel hydroxy(polyalkylenecarbonyloxy)alkyleneoxazolidines and bisoxazolidine isocyanate prepolymers.

The reaction of isocyanates with active hydrogen compounds such as amines and alcohols to form polyureas and polyurethanes has been greatly studied in the prior art, and this general class of polymers has been found to possess many useful properties. Since isocyanates generally react quickly and efficiently with active hydrogen compounds at room temperature, these two components usually must be mixed together only at the time and place at which reaction is desired. In previous approaches to making "one pot" compositions, in which the reacting materials are packaged together before using and later activated, relatively unreactive derivatives of isocyanates have been employed which regenerate the free isocyanate upon heating. Various catalysts are also often contained in these compositions to facilitate the regeneration of isocyanate. However, the heating process has several disadvantages, especially when the polyurea or polyurethane is to be used as a coating. For example, the size of the article to be coated or the nature of the material of which the article is made may preclude heating to the temperature necessary for polymerization to occur. Thus, it is extremely desirable to have polymer forming compositions which are stable on storage and which can be cured in the absence of any extensive heating and without the specific addition of other materials. Moreover, polyurea or polyurethane forming compositions having improved cure times would also be quite valuable.

It has now been found that compositions comprising a hydroxy(polyalkylenecarbonyloxy)alkyleneoxazolidine and a polyfunctional aliphatic or aromatic isocyanate will cure in the presence of water such as atmospheric moisture to afford tough and useful polymeric materials.

The hydroxy(polyalkylenecarbonyloxy)alkyleneoxazolidines (I, infra) employed in the novel hydrocurable compositions of this invention have the following structural formula:

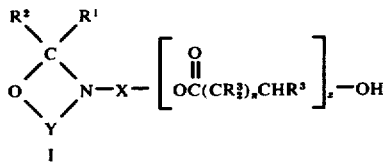

wherein $R^1$ is hydrogen, mononuclear aryl, for example, phenyl and the like, aralkyl, for example, benzyl and the like or alkyl, for example, alkyl of from 1-12 carbon atoms such as methyl, ethyl, n-propyl, n-butyl, pentyl, hexyl, heptyl, octyl, nonyl, decyl, undecyl, dodecyl and the like; $R^2$ is hydrogen or alkyl, for example, lower alkyl of from 1-4 carbon atoms such as methyl, ethyl, n-propyl, n-butyl and the like; or $R^1$ and $R^2$ are joined together with the carbon atom to which they are attached to form cycloalkyl of from 5-6 carbon atoms, such as cyclopentyl, cyclohexyl and the like; $R^3$ is hydrogen, alkyl, cycloalkyl, alkoxy or mononuclear aryl; Y is unsubstituted or substituted lower alkylene such as ethylene or propylene, wherein the substituents may be one or more radicals selected from alkyl, for example, alkyl of from 1-12 carbon atoms, aryl of 6-10 carbon atoms, aralkyl or alkanoyl of 7-12 carbon atoms. The $R^1$, $R^2$ and $R^3$ radicals may be further substituted with halo such as chloro, fluoro, bromo and the like, lower alkoxy, such as methoxy, ethoxy and the like, hydroxy, amino or nitro; X is substituted or unsubstituted lower alkylene such as ethylene, propylene, butylene and the like, wherein the substituent may be one or more alkyl radicals, for example, lower alkyl of from 1-6 carbon atoms; $n$ is an integer of at least 4, for example, 4-6, and $z$ is an integer of 1-50.

A wide variety of polyfunctional isocyanates, that is, isocyanates having at least two NCO groups, can be used in the compositions of the invention and substantially any isocyanate having two or more NCO groups which will react with an oxazolidine in the presence of moisture can be used. The isocyanates which are used in the compositions of the invention are well-known in the art.

Examples of the polyisocyanates which can be used in the compositions of the invention are aliphatic diisocyanates such as a diisocyanate derived from a 36 carbon diamine (DDI - General Mills, Inc.), 1,6-hexamethylene diisocyanate, 1,8-octamethylene diisocyanate, 1,12-dodecamethylene diisocyanate, 2,2,4-trimethylhexamethylene diisocyanate, and similar alkylene diisocyanates, 3,3'-diisocyanatodipropyl ether, 3-isocyanatomethyl-3,5,5-trimethylcyclohexylisocyanate, cyclopentylene-1,3-diisocyanate, cyclohexylene-1,4-diisocyanate, methyl 2,6-diisocyanatocaproate, and related isocyanates, bis(2-isocyanatoethyl)fumarate, 4-methyl-1,3-diisocyanatocyclohexane, trans-vinylene diisocyanate and similar unsaturated isocyanates, 4,4'-methylene-bis(isocyanatocyclohexane), and related isocyanates, menthane diisocyante, N,N',-N''-tris(6-isocyanatohexamethylene)biuret, and related isocyanates, bis(2-isocyanatoethyl)carbonate, and similar carbonate diisocyanates, as well as other known isocyanates derived from aliphatic polyamines, aromatic isocyanates such as tolylene diisocyanates, xylylene diisocyanates, dianisidine diisocyanate, 4,4'-diphenylmethane diisocyante, 1-ethoxy-2,4-diisocyanatobenzene, 1-chloro-2,4-diisocyanatobenzene, tris-(4-isocyanatophenyl)methane, naphthalene diisocyanates, fluorene diisocyanates, 4,4'-biphenyl diisocyanate; phenylene diisocyanates, 3,3'-dimethyl-4,4'-biphenyl diisocyanate, p-isocyanatobenzyl isocyanate, tetrachloro-1,3-phenylene diisocyanate, and related isocyanates, 2,4,6-tribromo-1,3-phenylene diisocyanate, bis(2-isocyanatoethyl)benzene, vinyl polymers containing isocyanatoethyl methacrylate as a monomer or comonomer, prepolymers of polyisocyanates with polyhydroxyl or polyamino compounds, such as prepolymers of 3-isocyanatomethyl-3,3,5-trimethylcyclohexylisocyanate, tolylene diisocyanate, menthane diisocyanate, 4,4'-methylene-bis(cyclohexylisocyanate), 2-isocyanatoethyl 6-isocyanatocaproate, 2-isocyanatoethyl 2-isocyanatopropionate and the like, with polyether polyols, polyester polyols, and the like. Preferred isocyanates of this invention include N,N'N''-tris-(6-isocyanatohexamethylene)biuret; 4,4'-methylene-bis(cyclohexylisocyanate), and aliphatic diisocyanate derived from a 36 carbon diamine, methylene-bis(4-phenylisocyanate); toluene diisocyanate, 3-isocyanatomethyl-3,5,5-trimethylcyclohexylisocyanate, 2-isocyanatoethyl-6-isocyanatocaproate or 2-isocyanatoethyl-2-isocyanatopropionate.

The preparation of the isocyanate prepolymers useful in the compositions of this invention is well-known in the art. The preparation of these prepolymers involves the reaction of the hydroxy terminated polyester, with a diisocyanate or polyisocyanate, using an excess of the isocyanate to yield an isocyanate terminated prepolymer product. A description of the techniques for preparing the isocyanate prepolymers is found in J. H. Saunders and K. C. Frisch, *Polyurethanes: Chemistry and Technology*, Part II, Interscience (New York, 1964); especially on pages 8 to 49.

Other polyfunctional isocyanates useful in the compositions of the invention are disclosed in U.S. Pat. Nos. 3,162,664; 3,427,346; 3,275,679; 3,352,830; 2,729,666; 2,768,154; 3,267,122; 3,281,378; 3,124,605 and 2,718,516.

A preferred embodiment of this invention is a hydrocurable coating composition comprising a hydroxy(polypentylenecarbonyloxy)ethyloxazolidine of the following formula:

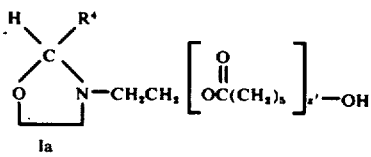

wherein $R^4$ is hydrogen or lower alkyl, such as methyl, ethyl, n-propyl, isopropyl, n-butyl and the like; $z'$ is an integer of 5-20 and an isocyanate selected from N,N',-N''-tris(6-isocyanatohexamethylene)biuret: 4,4'-methylene-bis-(cyclohexylisocyanate); a diisocyanate derived from a 36 carbon diamine (DDI), methylene-bis-(4-phenylisocyanate), toluene diisocyanate or isophorone diisocyanate. These compounds afford high solids containing compositions having an outstanding speed of cure and exceptional pot life.

The reaction of the hydroxy(polyalkylenecarbonyloxy) alkyleneoxazolidine (I, supra) with a diisocyanate can afford two products depending on the molar ratio of diisocyanate employed. To afford a monooxazolidine isocyanate polymer the molar ratio of the isocyanate functionality must be equal to or greater than one (1). Preferably the molar ratio of isocyanate functionality is in the range of from about 1 to about 3. The following equation illustrates this reaction.

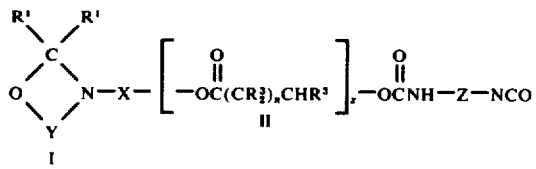

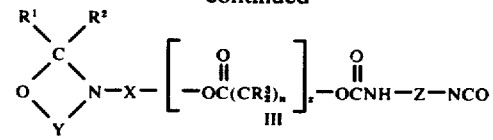

wherein $R^1$, $R^2$ and $R^3$, X, Y and $z$ are as defined above. $m$ is an integer equal to the valence of Z and Z is a polyvalent organic isocyanate reside derived from a known isocyanate. The polymer (III, supra), is a hydrocurable polymer.

When the molar ratio of a polyisocyanate (II, infra) is reduced to 0.5 or less, a chain extended, coupled bisoxazolidine (IV, infra) can be prepared which is an isocyanate prepolymer. The following formula illustrates this product:

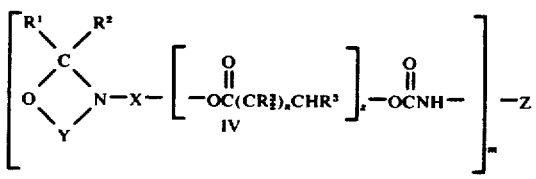

wherein $R^1$, $R^2$, $R^3$, X, Y, Z, $n$, $m$ and $z$ are as defined above. Polymer IV (supra) is a stable polyester urethane which can be further blended with additional di- or polyisocyanates to form hydrocurable compositions.

The hydroxy(polyalkylenecarbonyloxy)alkyleneoxazolidine (I, supra) is prepared by treating a hydroxyalkyleneoxazolidine (V, supra) with a lactone (VI, infra) having at least five (5) carbon atoms in the presence of a transesterification catalyst at a temperature in the range of from about 0° to 200° C. for a period of time from about 1 to about 24 hours. The following equation illustrates this process:

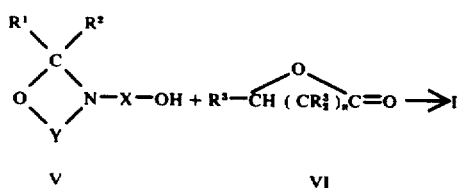

wherein $R^1$, $R^2$, $R^3$, X, Y and $n$ are as defined above. By employing a large molar excess of the lactone (VI), for example, at least 5 moles of lactone per mole of the hydroxyalkyleneoxazolidine (V), there is assured a complete reaction of the hydroxyalkyleneoxazolidine (V).

Catalysts which may be employed include the organometallic compounds, metals, metal hydrides, metal alkoxides, amines and the like. The preferred catalysts are metal alkoxides such as sodium methoxide and the like, tetrapropyl titanate, tetraalkylammonium alkoxides, such as tetraethylammonium ethoxide, and the like and alkyl tin oxides, esters and alkoxides such as dibutyltin oxide, dibutyltin dimethoxide, dibutyltin diacetate or dilaurate and the like.

The preparation of the hydroxyalkyleneoxazolidines (V, supra) is disclosed in U.S. Pat. No. 3,743,626 which patent is hereby incorporated by reference.

Examples of the lactones which may be employed include, for example, β-propiolactone, δ-valerolactone, ε-caprolactone, 7-hydroxyheptanoic acid lactone, 8-hydroxyoctanoic acid lactone, 12-hydroxydodecanoic acid lactone, 13-hydroxytridecanoic acid lactone, 14-hydroxytetradecanoic acid lactone, 15-hydroxypentadecanoic acid lactone, 16-hydroxyhexadecanoic acid lactone, 17-hydroxyheptadecanoic acid lactone; the α, α-dialkyl-β-propiolactones, for example, α,α-dimethyl-β-propiolactone, α,α-diethyl-β-propiolactone, α,α-dipropyl-β-propiolactone and the like; δ-valerolactones, wherein the alkyl is from 1–12 carbon atoms, such as isopropyl, butyl, hexyl, decyl, dodecyl and the like; dialkyl-δ-valerolactones in which the alkyl groups of from 1–12 carbon atoms are substituted on the same or different carbon atoms in the cyclic ring; the monoalkyl-, dialkyl-or trialkyl-ε-caprolactones, wherein alkyl is from 1–12 carbon atoms, the monoalkoxy- and dialkoxy-δ-valerolactones and ε-caprolactones, for example, the monomethoxy-, mono-ethoxy-, monoisopropoxy-, dimethoxy-, diethoxy and dibutoxy-δ-valerolactones, ε-caprolactones and the like. Further illustrative cyclic esters include 3-ethyl-2-keto-1,4-dioxane, γ-(1-isopropyl-4-methylcyclohexyl)-ε-caprolactone, 3-bromo-2,3,4,4-tetrahydrobenzoxepin-2-one, 2-(2'-hydroxyphenyl)-benzene carboxylic acid lactone, 10-hydroxyundecanoic acid lactone, 2,5,6,7-tetrahydrobenzoxepin-2-one, 9-oxabicyclo[5,2,2]undecan-8-one, 4-oxa-14-hydroxytetradecanoic acid lactone, α,α-bis(chloromethyl)-propiolactone, 1,4-dioxane-2-one, 3-n-propyl-2-keto-1,4-dioxane, 3-(2-ethylhexyl)-2-keto-1,4-dioxane, and the like. Illustrative subclasses of cyclic esters which are suitable in the process of the instant invention include the unsubstituted lactones and oxalactones which contain from 6 to 18 atoms in the lactone ring, preferably δ-valerolactone, ε-caprolactone, ketodioxanes and the like; the mono- and polyalkyl substituted lactones and oxalactones which contain from 6 to 8 atoms in the lactone ring, preferably, the mono- and poly lower alkyl ε-valerolactones, ε-caprolactones, and their corresponding oxalactones wherein the alkyls contain from 1 to 4 carbon atoms; mono- and polyalkoxy substituted lactones and oxalactones which contain from 6 to 8 atoms in the lactone ring, preferably the mono- and poly-lower alkoxy-δ-valerolactones, ε-caprolactones, and their corresponding oxalactones wherein the alkoxy contains from 1 to 4 carbon atoms.

The unsubstituted and substituted δ-valerolactones, δ-caprolactones L-enantholactones, and higher membered lactones, for example, mono- and polyalkyl substituted δ-valerolactones, mono- and polyalkoxy substituted δ-valerolactones, mono- and polycycloalkyl substituted δ-valerolactones, aryl substituted δ-valerolactones, mono- and polyhaloalkyl substituted δ-valerolactones, mono- and polyalkyl substituted ε-caprolactones, mono- and polyalkoxy ε-caprolactones, aryl substituted ε-caprolactones, mono- and polyhaloalkyl substituted ε-caprolactones, mono- and polyalkyl substituted L-enantholactones, and various other lactones described previously can be prepared by reacting the corresponding cyclic ketone with an anhydrous solution comprising peracetic acid and acetone. It is desirable to add the peracetic acid solution to an excess of the ketone, for example, a 5 to 1 molar ratio of ketone to peracetic acid, in a still kettle maintained under reflux. The pressure can be adjusted so as to provide a kettle temperature of about 70° C. Acetone, acetic acid by-product and minor amounts of ketone can be continuously removed throughout the addition period. Subsequently, the lactone product can be recovered from the still kettle by conventional techniques such as by distillation.

The reaction between the oxazolidines (I, supra) and the isocyanate component is initiated by water, for example, atmospheric moisture. A trace amount of atmospheric moisture is generally sufficient to initiate the polymerization reaction and cure the composition. If desired, water, for example, other than atmospheric, may be added to the compositions to effect cure, but this is not necessary. It is believed that the polymeric materials formed from the compositions of the invention result from the rapid hydrolysis of the oxazolidine which opens the oxazolidine ring at one of the bonds to the oxygen atom. The following reaction sequence illustrates the postulated path of the hydrolysis:

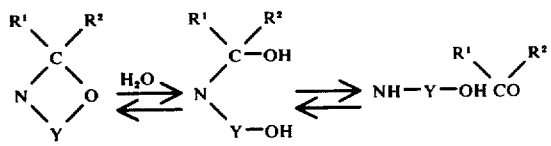

The amino alcohol produced has active hydrogen sites which react rapidly with an isocyanate. The isocyanate can react with either the amino group or the hydroxy group but is believed to be faster with the amino group.

Since the isocyanate is polyfunctional and the oxazolidine reacts in the presence of water as a polyfunctional compound, their reaction, as described above, will produce a highly polymeric material. Of course, a compound having more than one oxazolidine group will react as a polyfunctional material even if the isocyanate and oxazolidine are present in such proportions as to cause primary reaction during cure with the amine functionality only. While the hydrocuring reaction, that is, the hydrolysis and ensuing polymerization, will normally occur rapidly at ambient temperatures, elevated temperatures may facilitate reaction and curing under some conditions.

The hydrocuring reaction can be carried out with or without a catalyst. Under certain conditions, an acid catalyst, such as p-toluenesulfonic acid, dibutyltin octoate, zinc chloride, hydrogen chloride and the like, may be advantageously employed. The acid catalyst will generally be present in an amount of from about 0.001% to about 10% by weight based on the weight of oxazolidine, and preferably from about 1% to about 5% by weight.

The compositions of the invention need not contain a solvent, but an inert or relatively inert solvent can be added to the composition, if desired, either at the time of original formulation or at the time of use. The rate of the hydrolysis of the oxazolidine and the subsequent reaction with isocyanate can be influenced by the presence of a solvent. Solvents which are suitable for use in the compositions of the invention should be substantially free from active hydrogen atoms as determined by the Zerewitinoff method, described in Kohler et al., J. Am. Chem. Soc., 40, 2181–8 (1927), and should also be substantially anhydrous. Included among the solvents which can be used are toluene, xylene, liquid aliphatic hydrocarbons, isopropyl ether, ethyl acetate, β-ethoxyethyl acetate, methyl ethyl ketone and the like, as well as mixtures of such solvents. Pigments, dyes, fillers, antioxidants, antiozodants, stabilizers, flow control agents or other optional ingredients can also be included in the compositions of the invention.

The compositions of the invention can be used in forming films, fibers, paints, lacquers, varnishes, seamless flooring, caulks, as coatings, impregnants, adhesives for both natural and synthetic substrates, such as paper, textiles, wood, plastics, metal or leather and also as binders for non-woven fabrics. To prepare coatings and films, the compositions of the invention can be applied with or without solvent by casting permanently or removably onto a suitable substrate such as wood, metal, plastic, paper or leather.

The compositions of the invention provide an improved combination of increased pot life and increased curing speed with respect to those combinations which contain compounds having free amine groups.

Various embodiments of the compositions of the invention and the polymeric materials formed from them exhibit a number of desirable and advantageous properties. Some of the compositions can be sealed in a single package so that if moisture is excluded, undesirable thickening or gelling do not occur during storage. Even those compositions that are not extremely stable in one-pot formulations offer improved stability over conventional two-pot urethane systems. Since exposure to atmospheric moisture will effect cure, no additional materials need be mixed with these compositions at the time of use, thus facilitating greatly their handling. Furthermore, when no solvent is incorporated in the compositions, they are extremely high solids coating materials. When some of the compositions are used for the impregnation of leather, they provide significant improvements in break over known urethane systems.

The examples which follow illustrate the hydroxy (polyalkylenecarbonyloxy)alkyleneoxazolidines (I) of the invention and the methods by which they are prepared. However, the examples are illustrative only and it will be apparent to those having ordinary skill in the art that all of the products embraced by Formula I, supra, may also be prepared in an analgous manner by substituting the appropriate starting materials for those set forth in the examples.

EXAMPLE 1

3-[hydroxy(polypentylenecarbonyloxy)ethyl]oxazolidine (MW 1240)

To a flask equipped for stirring, addition, heating, reflux and automatic temperature control is charged hydroxyethyloxazolidine (HEOX, 1.5 mole, 175.5 g.), ε-caprolactone (3.0 mole, 342.0 g.) and dibutyltin oxide ($Bu_2SnO$, 0.75% on polyester, 7.73 g.). The flask charge is heated to 100° C. and held at that temperature while ε-Cl (4.5 mole, 513.0 g.) is added over a 60 minute period. After the addition is complete, the batch is held at 100° C. for 4 hours to complete reaction. The product 3-[hydroxy(polypentylene-carbonyloxy)ethyl]oxazolidine (MW 1240) is a fluid while hot but on cooling forms a waxy solid (acid 0.130 meg./g., amine 1.38 meq./g., GPC mol. wts. $M_w$ 1240, $M_n$ 770 $M_w/M_n$ 1.62, calcd. mol. wt. 687, equivalent weight for reaction with isocyanate 229 g./eq.

EXAMPLE 2

Hydrocurable composition of 3-[hydroxy(polypentylene-carbonyloxy)ethyl]oxazolidine (MW 1240) and DDI 3-[hydroxy(polypentylenecarbonyloxy)ethyl]oxazolidine (MW 1240) (0.01 eq.,2.29 g.) is dissolved in xylene (5.3 g.) and a diisocyanate derived from a 36 carbon diamine (DDI) (.01 eq.,3.00 g.) is added. After mixing, a 10 mil wet film is cast on a glass plate and is allowed to cure at room temperature (tack-free time 60 minutes, clear film, swelling by 2-ethoxyethyl acetate is light, pencil hardness <6B).

EXAMPLE 3

Hydrocurable composition of 3-[hydroxy(polypentylene-carbonyloxy)ethyl]oxazolidine and N,N',N''-tris(6-isocyanatohexamethylene)biuret 3-[hydroxy(polypentylenecarbonyloxy)ethyl]oxazolidine mol. wt. 1240 (0.01 eq., 2.29 g., is dissolved in xylene (3.6 g.) and N,N',N''-tris(6-isocyanatohexamethylene)biuret (0.01 eq., 2.50 g.) is added. After mixing, a 10 mil wet film is cast on a glass plate and allowed to cure at room temperature (tack-free time 10 minutes, clear film, swelling by 2-ethoxyethyl acetate is very slight, pencil hardness H).

EXAMPLE 4

Hydrocurable Composition of 3-[Hydroxy(polypentylene-carbonyloxy)ethyl]oxazolidine and 4,4'-methylene-bis(cyclohexylisocyanate)

3-[(Hydroxy(polypentylenecarbonyloxy)ethyl]oxazolidine (0.01 eq., 2.29 g.) is dissolved in xylene (3.6 g.) and 4,4'-methylenebis(cyclohexylisocyanate) (0.01 eq., 1.31 g.) is added. After mixing, a 10 mil. wet film is cast on a glass plate and allowed to cure at room temperature (tack-free time 60 minutes, clear film, swelling by 2-ethoxyethyl acetate is very slight, pencil hardness F).

EXAMPLE 5

Composition of 3-[Hydroxy(polypentylenecarbonyloxy)ethyl]oxazolidine and 4,4'-methylenebis(cyclohexylisocyanate A mixture of 3-[hydroxy(polypentylenecarbonyloxy)ethyl]oxazolidine (0.64 mole, 443.0 g.) is heated to 80° C. and then 4,4'-methylenebis(cyclohexylisocyanate) (0.32 mole, 83.8 g.) is added. The mixture exotherms to 113° C. and is allowed to cool with stirring to 100° C. over a 30 minute period. At room temperature this isocyanate coupled bisoxazolidine product forms a waxy solid (calcd. mol. wt. 1636, 409 g./eq. for reaction with isocyanate). The product is mixed with xylene and various di- and polyisocyanates to produce moisture curing coatings.

EXAMPLE 6

3-[Hydroxy(polypentylenecarbonyloxy)ethyl]oxazolidine and DDI

A mixture of 3-[hydroxy(polypentylenecarbonyloxy)ethyl]oxazolidine (1.50 mole, 1030.5 g.) is heated to 80° C. and DDI (0.75 mole, 450 g.) is added. The mixture exotherms to 98° C. and is allowed to cool with stirring to 80° C. over 30 minutes. At room temperature this isocyanate coupled bisoxazolidine product forms a waxy solid (calcd. mol. wt. 1976, 494 g./eq. for reaction with isocyanates).

EXAMPLE 7

Hydrocurable Composition of the bisoxazolidine of Example 6 and N,N',N''-tris(6-isocyanatohexamethylene)biuret The product of Example 6 (0.01 eq., 4.94 g.) is dissolved in xylene (7.5 g.) and N,N',N''-tris(6-isocyanatohexamethylene)biuret (0.01 eq., 2.50 g.) is added. After mixing, a 10 mil wet film is cast on a glass plate and allowed to cure at room temperature (tack-free time 15 minutes, clear film, swelling in 2-ethoxyethyl acetate light).

EXAMPLE 8

3-[Hydroxy(polypentylenecarbonyloxy)ethyl]oxazolidine (MW 1590)

To a flask equipped for stirring, addition, heating, reflux and automatic temperature control is added HEOX (0.4 mole, 46.8 g.), ε-caprolactone (3.2 mole, 364.8 g.) and $Bu_2SnO$ (1.0% on polyester, 4.14 g.). The mixture is heated to 100° C. and held there for 260 minutes while ε-caprolactone reacts. The product is a fluid while hot but on cooling forms a waxy solid (acid 0.091 meq./g., amine 0.936 meq./g., GPC mol. wt. $M_w$1590, $M_n$980, $M_w/M_n$ = 1.62, calcd. mol. wt. 1030, equivalent weight for reaction with isocyanate 343 g./3 g.).

EXAMPLE 9

Hydrocurable Composition of 3-[Hydroxy(polypentylene-carbonyloxy)ethyl]oxazolidine (MW 1590) and DDI 3-[Hydroxy(polypentylenecarbonyloxy)ethyl]oxazolidine (MW 1590) (0.01 eq. 3.43 g.) is dissolved in xylene (6.4 g.) and DDI (0.01 eq. 3.00 g.) is added. After mixing, a 10 mil film is cast on a glass plate and is allowed to cure at room temperature (tack-free time 60 minutes, hazy film, swelling by 2-ethoxyethyl acetate is light, pencil hardness <6B.

EXAMPLE 10

Hydrocurable Composition of 3-[Hydroxy(polypentylene-carbonyloxy)ethyl]oxazolidine (MW 1590) and N,N',N''-tris(6-isocyanatohexamethylene)biuret 3-[Hydroxy(polypentylenecarbonyloxy)ethyl]oxazolidine (MW 1590) (0.01 eq. 3.43 g.) is dissolved in xylene (5.0 g.) and N,N',N''-tris(6-isocyanatohexamethylene)biuret (0.01 eq. 2.50 g.) is added. After mixing, a 10 mil wet film is cast on a glass plate and allowed to cure at room temperature (tack-free time 10 minutes, clear film, swelling by 2-ethoxyethyl acetate very slight, pencil hardness F).

EXAMPLE 11

Hydrocurable Composition of 3-[Hydroxy(polypentylene-carbonyloxy)ethyl]oxazolidine (MW 1590) N,N',N''-tris(6-isocyanatohexamethylene)biuret 3-[Hydroxy(polypentylenecarbonyloxy)ethyl]oxazolidine (MW 1590) (0.01 eq. 3.43 g.) is dissolved in xylene (4.7 g.) and 4,4'-methylenebis(cyclohexylisocyanate) (0.01 eq.; 1.31 g.) is added. After mixing, a 10 mil wet film is cast on a glass plate and allowed to cure at room temperature (tack-free time 120 minutes, clear film, swelling by 2-ethoxyethyl acetate very slight, pencil hardness 3B).

EXAMPLE 12

Hydrocurable Composition of 3-[Hydroxy(polypentylenecarbonyloxy)ethyl]oxazolidine (MW 1590) and toluene diisocyanate 3-Hydroxy(polypentylenecarbonyloxy)ethyl]oxazolidine (MW 1590) (0.01 eq. 3.43 g.) is dissolved in xylene (4.4 g.) and toluene diisocyanate (0.01 eq. 0.9 g.) is added. After mixing, a 10 mil wet film is cast on a glass plate and allowed to cure at room temperature (tack-free time 60 minutes, clear film, swelling by 2-ethoxyethyl acetate slight).

EXAMPLE 13

3-[Hydroxy(polypentylenecarbonyloxy)ethyl]oxazolidine (MW 1257)

To a flask equipped for stirring, addition, heating, reflux and automatic temperature control is charged HEOX (0.09 mole, 105.3 g.) ε-caprolactone (1.8 mole, 205.2 g.) and $Bu_2SnO$ (0.75% on polyester, 8.49 g.). The flask is heated to 100° C. and held at that temperature while more ε-caprolactone (7.2 mole, 820.8 g.) is added over 60 minutes. The batch is held at 100° C. for 6 hours to complete reaction. The product hydroxy-(polypentylenecarbonyloxy)ethyloxazolidine is a fluid while hot but on cooling, forms a waxy solid (calcd. mol. wt. 1257, equivalent weight for reaction with isocyanate, 419 g./eq.

EXAMPLE 14

Bisoxazolidine of 3-[Hydroxy(polypentylenecarbonyloxy)ethyl]oxazolidine and 4,4'-methylenebis(cyclohexylisocyanate)

The bisoxazolidine of 3-[hydroxy(polypentylenecarbonyloxy)ethyl]oxazolidine 0.42 mole 531.9 g.) is heated to 80° C. 4,4'-methylenebis(cyclohexylisocyanate) (0.21 moles, 55.0 g.) is then added. The mixture exotherms to 101° C. and is held for 30 minutes to complete the reaction. At room temperature the product is a waxy solid (calcd. mol. wt. 2776, 694 g./eq. for reaction with isocyanates).

EXAMPLE 15

3-[Hydroxy(polypentylenecarbonyloxy)ethyl]oxazolidine (MW 2570)

To a flask equipped for stirring, addition, heating, reflux and automatic temperature control is added HEOX (0.60 mole, 70.2 g.) ε-caprolactone (1.2 mole, 136.8 g.) and $Bu_2SnO$ (0.75% of total polyester, 8.22 g.). The flask charge is heated to 100° C and held at that temperature while more ε-caprolactone (7.8 mole, 889.2 g.) is added over a 60 minute period. After the addition is complete, the batch is maintained at 100° C. for 6 hours to complete reaction. The product is a fluid while hot but on cooling forms a waxy solid (acid 0.09 meq./g., amine 0.523 meq./g., GPC mol. wts. Mw 2570 Mn 1690 $M_w/M_n$ 52; calcd. mol. wt. 1827. Equivalence for reaction with isocyanate 609 g./eq.

EXAMPLE 16

Hydrocurable Composition of
3-[Hydroxy(polypentylene-carbonyloxy)ethyl]oxazolidine and DDI 3-[Hydroxy(polypentylenecarbonyloxy)ethyl]oxazolidine (0.01 eq. 6.09 g.) is dissolved in xylene (9.0 g.) and DDI (0.01 eq. 3.00 g.) is added. After mixing, a 10 mil wet film is cast on a glass plate and is allowed to cure at room temperature (tack-free time 90 minutes, hazy film, swelling in 2-ethoxyethyl acetate is moderate with some lifting from glass, pencil hardness <6B).

EXAMPLE 17

Hydrocurable Composition of
3-[Hydroxy(polypentylenecarbonyloxy)ethyl]oxazolidine and
N,N',N''-bis(6-isocyanatohexamethylene)biuret Bisoxazolidine of 3-[hydroxy(polypentylenecarbonyloxy)ethyl]oxazolidine (0.01 eq. 6.09 g.) is dissolved in xylene (8.6 g.) and N,N',N''-bis(6-isocyanatohexamethylene)biuret (0.01 eq. 2.50 g.) is added. After mixing, a 10 mil wet film is cast on a glass plate and allowed to cure at room temperature (tack-free time 15 minutes, clear film, swelling in 2-ethoxyethyl acetate is very slight, pencil hardness <6B).

EXAMPLE 18

Hydrocurable Composition of
3-[Hydroxy(polypentylenecarbonyloxy)ethyl]oxazolidine and toluene diisocyanate 3-[Hydroxy(polypentylenecarbonyloxy)ethyl]oxazolidine (0.01 eq. 6.09 g.) is dissolved in xylene (7.0 g.) and toluene diisocyanate (0.01 eq. 0.9 g.) is added. After mixing, a 10 mil wet film is cast on a glass plate and is allowed to cure at room temperature (tack-free time 60 minutes, hazy film, swelling in 2-ethoxyethyl acetate slight).

EXAMPLE 19

Hydroxy(polypentylenecarbonyloxy)ethyloxazolidine and 4,4'-methylenebis(cyclohexylisocyanate)

Hydroxy(polypentylenecarbonyloxy)ethyloxazolidine 0.28 mole, 515.4 g.) is heated to 80° C. and 4,4'-methylenebis-(cyclohexylisocyanate) (0.14 mole, 36.7 g.) is added. The mixture exotherms to 92° C. and is held at 95°–100° C. for 30 minutes to complete reaction. At room temperature, this isocyanate coupled, bisoxazolidine product forms a waxy solid (calcd. mol. wt. 3916, 979/eq. for reaction with isocyanate). The product is mixed with xylene and various di- and polyisocyanates to produce moisture curing coatings.

EXAMPLE 20

3-[Hydroxy(polypentylenecarbonyloxy)ethyl]-2-isopropyloxazolidine (MW-730)

To a flask equipped for stirring, addition, heating, reflux and automatic temperature control is added 2-isopropyl-1-hydroxyethyloxazolidine (IPOX, as an 82.3% solution in xylene, 1.50 mole, 289.8 g.) and Bu₂SnO (0.25% on total polyester 2.73 g). The flask is heated to 125° C. and ε-caprolactone (7.5 mole, 855.0 g.) is added over a 60 minute period. When the addition is complete, the batch is held at 125° C. for 2 hours to complete the reaction. The product, 3-[hydroxy(-polypentylenecarbonyloxy)ethyl]-2-isopropyloxazolidine (Mw-730) is a fluid while hot but on cooling to room temperature forms a waxy solid (calcd. mol. wt. 730, solids 95.2%, equivalent weight as supplied for reaction with isocyanate, 255 g./eq.

EXAMPLE 21

Hydrocurable Composition of
3-[Hydroxy(polypentylenecarbonyloxy)ethyl]-2-isopropyloxazolidine and
N,N',N''-bis(6-isocyanatohexamethylene)biuret 3-[Hydroxy-(polypentylenecarbonyloxy)ethyl]-2-isopropyloxazolidine (0.01 eq., 2.55 g.) is dissolved in xylene (5.1 g.) and N,N',N''-bis(6-isocyanatohexamethylene)biuret (0.01 eq., 2.50 g.) is added. After mixing, a 10 mil wet film is cast on a glass plate and allowed to cure at room temperature (tack-free time 60 minutes, clear film, swelling by 2-ethoxyethyl acetate very slight, pencil hardness F).

EXAMPLE 22

Hydrocurable Composition of
3-[Hydroxy-(polypentylenecarbonyloxy)ethyl]-2-isopropyloxazolidine (Mw-730) and
4,4'-methylenebis(cyclohexylisocyanate)

3-[Hydroxy-(polypentylenecarbonyloxy)ethyl]-2-isopropyloxazolidine (Mw-730) (0.01 eq., 2.55 g.) is dissolved in xylene (3.9 g.) and 4,4'-methylenebis(cyclohexylisocyanate) (0.01 eq., 1.31 g.) is added. After mixing, a 10 mil wet film is cast on a glass plate and allowed to cure at room temperature (tack-free time 120 minutes, clear film, swelling with 2-ethoxyethyl acetate slight, pencil hardness F).

EXAMPLE 23

Bisoxazolidine
3-[Hydroxy-(polypentylenecarbonyloxy)ethyl]-2-isopropyloxazolidine (Mw-730) and
4,4'-methylenebis(cyclohexylisocyanate)

3-[Hydroxy-(polypentylenecarbonyloxy)ethyl]-2-isopropyloxazolidine (Mw-730) (0.716 mole, 547.5 g.) is heated to 100° C. and then 4,4'-methylenebis(cyclohexylisocyanate) (0.358 mole, 93.8 g.) is added. The mixture exotherms to 127° C. and is allowed to cool, with stirring, to 100° C. for 30 minutes. At room temperature, this isocyanate coupled, bisoxazolidine product is a waxy solid (calcd. mol. wt. 1720 solids, 96.0% eq./wt. as supplied for reaction with isocyanates 448 g./eq.). The product is mixed with xylene and various di- and polyisocyanates to produce moisture curing coatings and adhesives.

EXAMPLE 24

Bisoxazolidine of
3-[Hydroxy-(polypentylenecarbonyloxy)ethyl]-2-isopropyloxazolidine (Mw-730) and
N,N',N''-bis(6-isocyanatohexamethylene)biuret 3-[Hydroxy-(polypentylenecarbonyloxy)ethyl]-2-isopropyloxazolidine (Mw-730) (0.75 mole, 573.8 g.) is heated to 80° C. and then N,N',N''-bis(6-isocyanatohexamethylene)biuret (0.25 mole, 188.0 g.) is added. The mixture exotherms to 103° C. and is held at 100° C. with stirring for 30 minutes. At room temperature, this isocyanate coupled, bisoxazolidine polyester slowly forms a waxy solid (calcd. mol. wt. 1834, solids 90.3%, equivalent weight as supplied for reaction with isocyanate 508 g./eq.). The product is mixed with xylene and various di- and polyisocyanates to produce moisture curing coatings.

EXAMPLE 25

3-[Hydroxy-(polypentylenecarbonyloxy)ethyl]-2-isopropyloxazolidine (Mw 1072)

To a flask equipped for stirring, addition, heating, reflux, and automatic temperature control is added IPOX (0.40 mole, 78.1 g.), ε-caprolactone (3.2 mole, 364.8 g.) and Bu$_2$SnO (1% on polyester, 4.14 g.). The mixture is heated to 100° C. and held there for 8 hours. The product is a fluid while hot but on cooling forms a waxy solid (calcd. mol. wt. 1072, solids 96.7%, equivalent weight as supplied for reaction with isocyanates 369 g./eq.).

EXAMPLE 26

Hydrocurable Composition of 3-[Hydroxy-(polypentylenecarbonyloxy)-2-isopropylethyloxazolidine and DDI 3-[Hydroxy-(polypentylenecarbonyloxy)ethyl]-2-isopropyloxazolidine (0.01 eq., 3.69 g.) is dissolved in xylene (6.7 g.) and DDI (0.01 eq., 3.00 g.) is added. After mixing, a 10 mil wet film is cast on a glass plate and is allowed to cure at room temperature (tack-free time 240 minutes, clear film, swelling by 2-ethoxyethyl acetate moderate, pencil hardness < 6B).

EXAMPLE 27

Hydrocurable Composition of 3-[Hydroxy-(polypentylenecarbonyloxy)ethyl]-2-isopropyloxazolidine (Mw 1072) and N,N',N''-tris(6-isocyanatohexamethylene)-biuret 3-[Hydroxy-(polypentylenecarbonyloxy)ethyl]-2-isopropyloxazolidine (Mw 1072) (0.01 eq., 3.69 g.) is dissolved in xylene (6.2 g.) and N,N',N''-tris(6-isocyanatohexamethylene) biuret (0.01 eq., 2.50 g.) is added. After mixing, a 10 mil wet film is cast on a glass plate and allowed to cure at room temperature (tack-free time 30 minutes, clear film, swelling by 2-ethoxyethyl acetate very slight, pencil hardness F).

EXAMPLE 28

3-[Hydroxy-(polypentylenecarbonyloxy)ethyl]-2-isopropyloxazolidine (Mw 1072) and 4,4'-methylenebis-(cyclohexylisocyanate)

3-[Hydroxy-(polypentylenecarbonyloxy)ethyl]-2-isopropyloxazolidine (Mw 1072) (0.01 eq., 3.69 g.) is dissolved in xylene (5.0 g.) and 4,4'-methylenebis(cyclohexylisocyanate) (0.01 eq., 1.31 g.) is added. After mixing, a 10 mil wet film is cast on a glass plate and allowed to cure at room temperature (tack-free time 120 minutes, clear film, swelling with 2-ethoxyethyl acetate slight, pencil hardness F).

EXAMPLE 29

Hydrocurable Composition of 3-[Hydroxy-(polypentylenecarbonyloxy)ethyl]-2-isopropylethyloxazolidine (Mw 1072) and toluene diisocyanate 3-[Hydroxy-(polypentylenecarbonyloxy)ethyl]-2-isopropyloxazolidine (Mw 1072) (0.01 eq., 3.69 g.) is dissolved in xylene (4.6 g.) and toluene diisocyanate (0.01 eq., 0.9 g.) is added. After mixing, a 10 mil wet film is cast on a glass plate and allowed to cure at room temperature (tack-free time 30 minutes, clear film, swelling with 2-ethoxyethyl acetate slight).

EXAMPLE 30

Bisoxazolidine of 3-[Hydroxy-(polypentylenecarbonyloxy)ethyl]-2-isopropyloxazolidine (Mw 1300)

To a flask equipped for stirring, addition, heating, reflux and automatic temperature control is added IPOX (0.8 mole, 154.6 g.) and Bu$_2$SnO (0.25%) on polyester, (26.0 g.). The flask is heated to 125° C. and ε-caprolactone (8.0 mole, 9.12 g.) is added over a 60 minute period. When the addition is complete, the batch is held at 125° C. for 10 more minutes to ensure a complete reaction. The product is a waxy solid (calcd. mol. wt. 1300, solids 97.2%, equivalent weight as supplied for reaction with isocyanate, 445 g./.eq.). The product is mixed with xylene and various di- and polyisocyanates to produce moisture curing coatings.

EXAMPLE 31

Bisoxazolidine of 3-[Hydroxy-(polypentylenecarbonyloxy)ethyl]-2-isopropyloxazolidine (Mw 730) and 4,4'-methylenebis(cyclohexylisocyanate)

3-[Hydroxy-(polypentylenecarbonyloxy)ethyl]-2-isopropyloxazolidine (Mw-730) (0.374 moles, 499.2 g.) is heated to 98° C. and then 4,4'-methylenebis(cyclohexylisocyanate) (0.187 mole, 49.0 g.) is added. The mixture exotherms to 117° C. and is allowed to cool with stirring to 100° C. over 30 minutes. At room temperature this isocyanate coupled, bisoxazolidine product is a waxy solid (calcd. mol. wt. 2860, solids 97.5% eq. wt. as supplied for reaction with isocyanates 733 g./eq.). The product is mixed with xylene and various di- and polyisocyanates to produce moisture curing coatings.

EXAMPLE 32

3-[Hydroxy-(polypentylenecarbonyloxy)ethyl]-2-isopropyloxazolidine (Mw 1860)

To a flask equipped for stirring, addition, heating, reflux and automatic temperature control is added IPOX (0.578 mole, 112.8 g.) and Bu$_2$SnO (0.2% on polyester, 2.75 G). The flask is heated to 125° C. and ε-caprolactone (8.67 mole, 988.4 g.) is added over a 90 minute period. When the feed is complete the batch is held at 125° C. for 60 minutes to complete the reaction. The product is solid (calcd. mol. wt. 1860, solids 98.1%, equivalent weight as supplied for reaction with isocyanates 635 g./eq.).

EXAMPLE 33

Bisoxazolidine of 3-[Hydroxy-(polypentylenecarbonyloxy)ethyl]-2-isopropyloxazolidine (Mw 1860) and 4,4'-methylenebis(cyclohexylisocyanate)

3-[Hydroxy-(polypentylenecarbonyloxy)ethyl]-2-isopropyloxazolidine (Mw 1860) (0.28 mole, 534.0 g.) is heated to 100° C. and then 4,4-methylenebis(cyclohexylisocyanate) (0.14 mole, 36.7 g.) is added. The mixture exotherms to 112° C. and is allowed to cool with stirring to 100° C. for 30 minutes. At room temperature this isocyanate coupled, bisoxazolidine product is a waxy solid (calcd. mol. wt. 4000, solids 98.2% eq. wt. 1018 g./eq.). The product is mixed with xylene and various di- and polyisocyanates to produce moisture curing coatings.

EXAMPLE 34

3-[Hydroxy-(polybutylenecarbonyloxy)ethyl]-2-isopropyloxazolidine (Mw 3945)

To a flask equipped for stirring, addition, heating, reflux and automatic temperature control is added IPOX (0.20 mole, 39.6 g.) and Bu$_2$SnO (0.25% on polyester, 0.92 g.). The flask is heated to 125° C. and a solution of ε-caprolactone (2.6 mole, 296.4 g.) and valerolactone (0.4 mole, 40.0 g.) is added over a 60 minute period. When the feed is complete, the batch is held at 125° C. for 90 minutes to complete reaction. The flask is cooled to 100° C. and then 4,4'-methylenebis(cyclohexylisocyanate) (0.10 mole, 26.2 g.) is added. The reaction exotherms to 113° C. and is allowed to cool with stirring to 100° C. for 30 minutes. At room temperature this isocyanate coupled, bisoxazolidine product is a waxy solid (calcd. mol. wt. 3945, solids 98.3% equ. wt. as supplied for reaction with isocyanates 1005 g./eq.). The product is mixed with xylene and various di- and polyisocyanates to produce moisture curing coatings.

EXAMPLE 35

Hydrocurable Composition of
3-[Hydroxy(polypentylenecarbonyloxy)propyl]tetrahydro-1,3-oxazine and
N,N',N''-tris-(6-isocyanatohexamethylene)biuret Step A 3-(β-hydroxypropyl)tetrahydro-1,3-oxazine To a glass reaction vessel equipped with stirrer, thermometer, and condenser fitted with a water trap is added di-(3-hydroxypropyl) amine (3.0 mole, 399 g.) and toluene (500 g.). Paraformaldehyde (3.15 mole, 90% pure, 105 g.) is weighed out and about 1/3 is added to the amine solution. The resulting mixture is stirred and heated to 90° C. while slowly adding the remaining paraformaldehyde in about 70 minutes. The reaction is heated to reflux and the water separated. After 4 hours, a total of 63 ml. of water is removed. Toluene is removed at reduced pressure. The residue is distilled at high vacuum to yield 3-(β-hydroxypropyl)-tetrahydro-1,3-oxazine.

Step B

Hydrocurable composition of
3-[hydroxy(polypentylenecarbonyloxy)propyl]tetrahydro-1,3-oxazine and
N,N'-N''-tris-(6-isocyanatohexamethylene)biuret To a flask equipped for stirring, addition, heating, reflux and automatic temperature control is charged 3-(hdroxypropyl)tetrahydro-1,3-oxazine (0.9 mole, 130.5 g.), ε-caprolactone (1.8 mole, 205.2 g.) and Bu$_2$SnO (0.75% on polyester, 8.6 g.). The flask is heated to 100° C. and held at that temperature while ε-caprolactone (7.2 mole, 820.8 g.) is added over a 60 minute period. After the feed is complete the batch is held at 100° C. for 6 hours to complete the reaction. The product 3-[hydroxy(polypentylenecarbonyloxy)-propyl]tetrahydro-1,3-oxazine is a fluid while hot but on cooling forms a waxy solid (calcd. mol. wt. 1285, equivalent weight for reaction with isocyanate, 426 g./eq.). The product (0.5 mole) is mixed with xylene and to produce a moisture curing coating.

EXAMPLE 36

Bisoxazine of
3-[Hydroxy(polypentylenecarbonyloxy)propyl]tetrahydro-1,3-oxazine

3-[Hydroxy(polypentylenecarbonyloxy)propyl]tetrahydro-1,3-oxazine (0.42 mole, 539.7 g.) is melted and heated to 80° C. and 4,4'-methylenebis(cyclohexylisocyanate) (0.21 mole, 55.0 g.) is added. The mixture exotherms to 101° C. and is held at 100° C. for 30 minutes to complete the reaction. At room temperature this isocyanate coupled, bis(tetrahydro-1,3-oxazine) is a waxy solid (calcd. mol. wt. 2832, 708 g./eq. for reaction with isocyanate). The product is mixed with various di- and polyisocyanates to produce moisture curing coatings.

By treating a 2-(R$^2$) hydroxyethyloxazolidine (1 mole) with ε-caprolactone ("A" moles) in the presence of a catalyst a correspondingly substituted 2-(R$^2$)hydroxy(polypentylenecarbonyloxy)ethyloxazolidine is obtained which product when reacted with one or more equivalents of an isocyanate affords the correspondingly substituted hydrocurable composition. Table I, below, illustrates the R$^2$ substituent, the number of moles of ε-caprolactone ("A"), the amount and type of catalyst, the temperature, the reaction time, and the isocyanate employed. Also, the molecular weight and equivalent weight of the hydrocurable composition, when obtained, are reported.

The following is an explanation of the isocyanates represented by Roman numerals and of other various symbols employed in the tables.

1. I' is diisocyanate having a 36 carbon diamine (DDI)
2. II' is 4,4'-methylenebis(cyclohexylisocyanate)
3. III' is methylene-bis(4-phenylisocyanate)
4. IV' is toluene diisocyanate
5. V' is 3-isocyanatemethyl-3,5,5-trimethylcyclohexylisocyanate
6. VI' is N,N',-bis(6-isocyanathohexamethylene)biuret
7. HEOX is N-hydroxyethyloxazolidine
8. IPOX is 2-isopropyl-N-hydroxyethyloxazolidine
9. OX indicates an oxazolidine
10. IC indicates an isocyanate

TABLE 1

| Ex. No. | R$^2$ | "A" moles | Catalyst (mole %) | Temp. °C. | Reaction Time (hrs.) | Isocyanate | Product MW | EaW |
|---|---|---|---|---|---|---|---|---|
| 37 | H | 5 | Bu$_2$SnO—4 | 100° | 6 | — | 1240 | — |
| 38 | H | 8 | " | " | 4 | — | 1590 | — |
| 39 | H | 15 | " | " | 12 | — | 2750 | — |
| 40 | H | 5 | " | " | 6 | — | — | — |
| 41 | H | 8 | " | " | 8 | — | — | — |
| 42 | —CH(CH$_3$)$_2$ | 5 | " | " | 6 | — | — | — |
| 43 | " | 8 | " | " | 8 | — | — | — |
| 44 | " | 15 | Bu$_2$SnO—5 | 125°–150° | 1 | I | 4300 | 1488 |
| 45 | " | " | " | " | " | II | 4000 | 1404 |
| 46 | " | " | " | " | " | III | — | — |

TABLE 1-continued

| Ex. No. | R² | "A" moles | Catalyst (mole %) | Temp. °C. | Reaction Time (hrs.) | Isocyanate | Product MW | EaW |
|---|---|---|---|---|---|---|---|---|
| 47 | " | " | " | " | " | IV | 3910 | 1380 |
| 48 | " | " | " | " | " | V | 3960 | 1394 |
| 49 | " | " | " | " | " | VI | 6170 | 1465 |
| 50 | " | " | Bu₂SnO—0.25 | 125° | 2.5 | — | 1860 | 635 |
| 51 | " | " | " | " | " | II' | 4000 | 1018 |
| 52 | " | 10 | " | " | 2 | — | 1300 | 445 |
| 53 | " | " | " | " | " | II' | 2860 | 733 |
| 54 | " | 5 | " | " | 3 | — | 730 | |
| 55 | " | " | " | " | " | II' | 1720 | 448 |
| 56 | " | 5 | " | " | " | VI' | 2754 | 508 |
| 57 | " | 13 | " | " | 2.5 | II' | 3945 | 1005 |
| 58 | " | 5 | NaOMe—0.25 | " | 8 | VI' | 1720 | 448 |

Films were made with a selection of isocyanates as indicated in the following Tables II and III and rudimentary properties determined. Table II summarizes the results when the hydroxyoxazolidine functional compounds are employed and Table III summarizes the results when the bisoxazolidine compounds are employed. The oxazolidine/ε-caprolactone//isocyanate hydrocurable composition afford high solids, long pot life resins which cure in the presence of atmospheric moisture to afford attractive, tough, solid resistant coatings as shown by the viscosity, tack-free time and film properties of the polymers.

Improved solution stability without an increase in tack-free time is realized with the bisoxazolidine (i.e., isocyanate coupled) resins. Similar results are observed Pencil hardness scale extends from 6B (softest) to 5B, 4B, 3B, 2B, B. HB, F, H, 2H, 3H, 4H, 5H, 6H, and 9H (hardest). The point of the pencil is rubbed down on flint paper to a flat surface. The pencil is held at 45° to the surface to be tested and then pushed across the surface. The rating is the hardest pencil that does not break the film.

Garnder-Holdt Viscosity is a bubble rise comparison viscosity. The sample to be tested is placed in a standard viscosity tube. The sample is then compared to a series of standard liquids with assigned letter values. The viscosity of the sample is the letter value of the standard with the same bubble rise rate. The scale of the standards runs from A-6 (lowest viscosity) to Z-10 (highest).

TABLE II (Oxazolidine/ε-Caprolactone//Isocyanate Polymers)
(eq. polyester/1 eq. isocyanate cast from xylene at 50% solids)

| Film No. | Composition ε-Caprolactone (moles)/OX (1 mole) | IC² | Viscosity (GH after × Hrs.)¹ | | | | | Tack Free Min. | Film Properties | | |
|---|---|---|---|---|---|---|---|---|---|---|---|
| | | | 1 | 4 | 22 | 48 | 144 | | Appearance | Swelling² | Hardness |
| 1A | 5/HEOX | I' | A2 | A2 | A2 | A1 | B | 60 | clear | light | <6B |
| 2A | 8/HEOX | " | A2 | A1 | A1 | A1 | C | 60 | hazy | light | " |
| 3A | 15/HEOX | " | C | D | E | F | N | 90 | " | mod. and lifting | |
| 4A | 5/IPOX | " | A3 | A3 | A3 | A3 | A3 | 240 | clear | swollen | " |
| 5A | 8/IPOX | " | A2 | A2 | A2 | A2 | A2 | 240 | " | moderate | " |
| 6A | 5/HEOX | VI' | S | W | ∞ | — | — | 10 | " | v. slight | H |
| 7A | 8/HEOX | " | T | X | ∞ | — | — | 10 | " | " | F |
| 8A | 15/HEOX | " | ∞ | — | — | — | — | 15 | " | " | <6B |
| 9A | 5/IPOX | " | D | D | E | E | G | 60 | " | " | F |
| 10A | 8/IPOX | " | M | P | R | S | W | 30 | " | " | F |
| 11A | 8/HEOX | I' | A4 | A2 | B | D | I | >24 hrs. | v. poor | moderate | — |
| 12A | 8/HEOX | VI' | A | ∞ | — | — | — | 120 | clear | slight | <6B |
| 13A | 5/HEOX | II' | A3 | A3 | A3 | — | A3 | 60 | " | v. slight | F |
| 14A | 8/HEOX | " | A3 | A3 | A3 | — | A2 | 120 | " | " | 6B |
| 15A | 5/IPOX | " | A4 | A4 | A4 | — | A4 | 120 | " | slight | F |
| 16A | 8/IPOX | " | A4 | A4 | A4 | — | A3 | 120 | " | " | F |

| Film No. | Composition ε-Caprolactone (moles)/OX (1 mole) | IC | Viscosity (GH after × Hrs.)¹ | | | | | Tack Free Min. | Film Properties | | |
|---|---|---|---|---|---|---|---|---|---|---|---|
| | | | 1 | 4 | 22 | 48 | 144 | | Appearance | Swelling² | Hardness |
| 17A | 5/HEOX | IV' | A4 | A4 | ∞ | — | — | 30 | clear | slight | — |
| 18A | 5/HEOX | III' | T | ∞ | — | — | — | 15 | " | " | — |
| 19A | 8/HEOX | IV' | A3 | A3 | A3 | A2 | ∞ | 30 | " | " | — |
| 20A | 8/HEOX | III' | G | ∞ | — | — | — | 15 | " | " | — |
| 21A | 15/HEOX | IV' | A | A | B | B | ∞ | 60 | hazy | " | — |
| 22A | 15/HEOX | III' | V | X | ∞ | — | — | 15 | clear | " | — |
| 23A | 5/IPOX | IV' | A4 | A4 | A4 | A4 | A2 | 30 | " | " | — |
| 24A | 5/IPOX | III' | B | D | ∞ | — | — | 15 | " | " | — |
| 25A | 8/IPOX | IV' | A4 | A4 | A4 | A4 | A3 | 30 | " | " | — |
| 26A | 8/IPOX | III' | B | K | ∞ | — | — | 15 | " | " | — |

¹Solution sealed in viscosity tubes under N₂
²After 30 minutes exposure to 2-hydroxyethyl acetate at room temperature with a selection of di- and triisocyanates.

TABLE III (Oxazolidine/ε-Caprolactone/Isocyanate//Isocyanate Polymers)
(1 eq. coupled polyester/1 eq. isocyanate cast from xylene at 50% solids)

| Film No. | Polyester ε-Caprolactone (mole) | OX | IC | Isocyanate | Viscosity (GH after × hrs)¹ | | | | | Tack Free (Min.) | Film Properties | |
|---|---|---|---|---|---|---|---|---|---|---|---|---|
| | | | | | 1 | 4 | 22 | 48 | 144 | | Appearance | Swelling² |
| A | 5 | HEOX | I' | I' | A1 | — | A | A | D | 45 | clear | moderate |

TABLE III-continued (Oxaxolidine/ε-Caprolactone/Isocyanate//Isocyanate Polymers)
(1 eq. coupled polyester/1 eq. isocyanate cast from xylene at 50% solids)

| Film No. | Polyester ε-Caprolactone (mole) | OX | IC | Isocyanate | Viscosity (GH after × hrs)[1] | | | | | Tack Free (Min.) | Film Properties Appearance | Swelling[2] |
|---|---|---|---|---|---|---|---|---|---|---|---|---|
| | | | | | 1 | 4 | 22 | 48 | 144 | | | |
| B | 5 | " | " | " | I | — | S | W | ∞ | 15 | " | |
| C | 15 | IPOX | I' | II' | A | A | A | A | A | 60 | hazy | slight |
| D | " | " | II' | " | B | B | B | B | B | 60 | " | " |
| E | " | " | IV' | " | A | A | A | A | A | 60 | " | " |
| F | " | " | V' | " | B | B | B | B | B | 60 | " | " |
| G | " | " | VI' | " | I | I | I | I | I | 60 | " | " |

[1]Solutions sealed in viscosity tubes under N₂
[2]After 30 minute exposure to 2-hydroxyethyl acetate at room temperature

What is claimed is:

1. A compound of the formula:

wherein $R^1$ is hydrogen, mononuclear aryl, aralkyl or alkyl; $R^2$ is hydrogen or alkyl or $R^1$ and $R^2$ are joined together with the carbon atom to which they are attached to form cycloalkyl; $R^3$ is hydrogen, alkyl, cycloalkyl, alkoxy or mononuclear aryl; $R^1$, $R^2$ and $R^3$ may be substituted with halo, lower alkoxy, hydroxy, amino or nitro; Y is unsubstituted or substituted lower alkylene; X is substituted or unsubstituted lower alkylene; n is an integer of at least 4; z is an integer of 1–50 and Z is a polyvalent organic isocyanate residue.

2. A compound according to claim 1 of the formula:

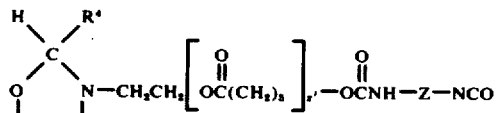

wherein $R^4$ is hydrogen or lower alkyl; z' is an integer of 5–20 and Z is a polyvalent organic isocyanate residue.

3. A compound of the formula:

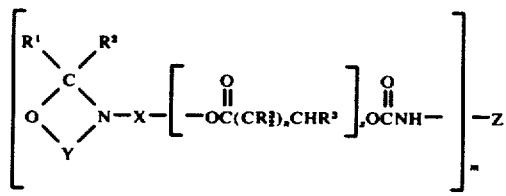

wherein $R^1$ is hydrogen, mononuclear aryl, aralkyl or alkyl; $R^2$ is hydrogen or alkyl or $R^1$ and $R^2$ are joined together with the carbon atom to which they are attached to form cycloalkyl; $R^3$ is hydrogen, alkyl, cycloalkyl, alkoxy or mononuclear aryl; $R^1$, $R^2$ and $R^3$ may be substituted with halo, lower alkoxy, hydroxy, amino or nitro; Y is unsubstituted or substituted lower alkylene; X is substituted or unsubstituted lower alkylene; n is an integer of at least 4, z is an integer of 1–50, Z is a polyvalent organic isocyanate residue and m is an integer equal to the valence of Z.

4. A compound according to claim 3 having the formula:

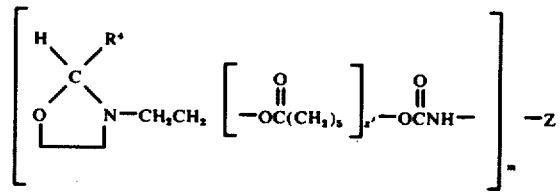

wherein $R^4$ is hydrogen or lower alkyl; z' is an integer of 5–20, Z is a polyvalent organic isocyanate residue, and m is an integer of two or three.

5. A compound of the formula:

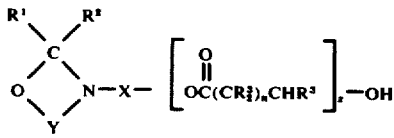

wherein $R^1$ is hydrogen, mononuclear aryl, aralkyl or alkyl; $R^2$ is hydrogen or alkyl or $R^1$ and $R^2$ are joined together with the carbon atom to which they are attached to form cycloalkyl; $R^3$ is hydrogen, alkyl, cycloalkyl, alkoxy or mononuclear aryl; $R^1$, $R^2$ and $R^3$ may be substituted with halo, lower alkoxy, hydroxy, amino or nitro; Y is unsubstituted or substituted lower alkylene; X is substituted or unsubstituted lower alkylene; n is an integer of at least 4 and z is an integer of 1–50.

6. A compound according to claim 5 of the formula:

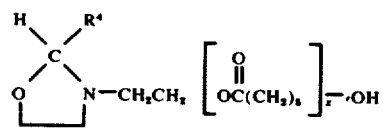

wherein $R^4$ is hydrogen or lower alkyl and z' is an integer of 5–20.

* * * * *